(12) United States Patent
Corma Canos et al.

(10) Patent No.: US 8,187,469 B2
(45) Date of Patent: *May 29, 2012

(54) SEPARATION OF FLUIDS USING ZEOLITE ITQ-32

(75) Inventors: Avelino Corma Canos, Valencia (ES); Fernando Rey Garcia, Valencia (ES); Susana Valencia Valencia, Valencia (ES)

(73) Assignees: Consejo Superior de Investigaciones Cientificas, Madrid (ES); Universidad Politecnica de Valencia, Valencia (ES)

( * ) Notice: Subject to any disclaimer, the term of this patent is extended or adjusted under 35 U.S.C. 154(b) by 676 days.

This patent is subject to a terminal disclaimer.

(21) Appl. No.: 11/989,330

(22) PCT Filed: Jul. 24, 2006

(86) PCT No.: PCT/ES2006/070113
§ 371 (c)(1),
(2), (4) Date: Mar. 23, 2009

(87) PCT Pub. No.: WO2007/012690
PCT Pub. Date: Feb. 1, 2007

(65) Prior Publication Data
US 2009/0202416 A1    Aug. 13, 2009

(30) Foreign Application Priority Data
Jul. 25, 2005  (ES) .................. 200501918

(51) Int. Cl.
| | | |
|---|---|---|
| B01D 15/00 | (2006.01) |
| B01D 15/04 | (2006.01) |
| B01D 53/22 | (2006.01) |
| B01D 59/12 | (2006.01) |
| B01D 53/02 | (2006.01) |
| B01D 59/26 | (2006.01) |
| B01D 47/00 | (2006.01) |
| B01D 53/14 | (2006.01) |
| B01J 39/00 | (2006.01) |
| B01J 49/00 | (2006.01) |
| C02F 1/42 | (2006.01) |
| C02F 1/28 | (2006.01) |
| C07C 7/144 | (2006.01) |
| C01B 33/36 | (2006.01) |
| C07C 7/12 | (2006.01) |
| C01B 39/00 | (2006.01) |
| C01B 21/00 | (2006.01) |
| C01F 7/00 | (2006.01) |

(52) U.S. Cl. ............................................... 210/690
(58) Field of Classification Search .................. 210/660, 210/670, 690, 691, 310 Z; 95/45, 90, 96, 95/232, 237, 240, 902; 585/818, 820; 423/718, 423/351

See application file for complete search history.

(56) References Cited

U.S. PATENT DOCUMENTS
6,488,741 B2 * 12/2002 Olson ............................ 95/144
7,582,278 B2 *  9/2009 Corma Canos et al. ...... 423/718

* cited by examiner

*Primary Examiner* — Nam Nguyen
*Assistant Examiner* — Nader Hossaini
(74) *Attorney, Agent, or Firm* — Wenderoth, Lind & Ponack, L.L.P.

(57) ABSTRACT

The invention relates to a method of separating fluids from mixtures using a zeolite known as ITQ-32 consisting of a two-dimensional pore system comprising channels with openings formed by 8 tetrahedra which are interconnected by channels with openings formed by 12 tetrahedra. The inventive method comprises at least the following steps: a) the zeolite ITQ-32 material is brought into contact with the mixture of fluids, b) one or more of the components are adsorbed in the zeolite ITQ-32 material, c) the non-adsorbed components are extracted, and d) one or more of the components adsorbed in the zeolite ITQ-32 material are recovered.

39 Claims, 5 Drawing Sheets

SEPARATION OF FLUIDS USING ZEOLITE ITQ-32

This application is a U.S. national stage of International Application No. PCT/ES2006/070113 filed Jul. 24, 2006.

TECHNICAL FIELD OF THE INVENTION

The present invention pertains to the technical field of microporous crystalline zeolite materials useful as adsorbents in processes of adsorption and separation of mixtures of fluids.

STATE OF THE ART PRIOR TO THE INVENTION

Light olefins are generally obtained by catalytic cracking of gas-oil, catalytic steam cracking or by means of what is known as the MTO (Methanol-to-olefins) process. In all of these processes, mixtures of different hydrocarbons are obtained which include linear and branched olefins and paraffins of different molecular weights, said mixture therefore being put through distilling processes in order to obtain the pure hydrocarbons. The particular case of the purification of light olefins by means of distilling processes is especially difficult due to the relatively low boiling points of these olefins and their similarity with those of the corresponding paraffins. This is especially true in the case of propylene and propane. These problems condition the design of the distilling plants to a major degree and inevitably redound in high energy consumption in the process of obtaining olefins. Nevertheless, the separation of short-chain olefins has a major economic impact, given that they are employed in different processes in which high purity is required. Specifically, ethylene and propylene are the raw materials employed in the production of plastics and many other chemical compounds. Thus, ethylene is the base reagent for the production of polyethylene, ethylene oxide, chlorovinyl and ethyl-benzene, among others. Propylene is used for producing polypropylene, propylene oxide, acrylonitrile, etc.

It is known that the use of molecular screens and particularly zeolites is useful in the different hydrocarbon separation processes. Thus, linear paraffins can be separated from branched paraffins by employing zeolites having channels which are accessible by way of windows formed by eight (8) tetrahedral. However, when there are olefins in the current of hydrocarbons, these olefins tend to react on the acid centers of the zeolites, giving rise to polymerization by-products on the interior of the zeolite channels. These by-products larger in kinetic diameter cannot diffuse outward toward the outside of the zeolite causing the blocking of its pores and therefore reducing its effectiveness in the separation processes.

The acid properties of the zeolites stem from the presence of trivalent elements in their composition, which generate a negative charge in the microporous network which is compensated by cations (generally alkaline, alkaline-terrous, protons or organic cations) which are situated on the interior of the channels and cavities of the zeolites. These compensating cations are responsible for the acid properties of these materials, particularly when the cations are protons. In this case, the acid strength of the zeolites can be comparable to that of concentrated sulfuric acid. The presence of inorganic cations, such as $Na^+$, $K^+$, $Ca^{2+}$, etc. . . . , generates weak Lewis-type acid centers and are responsible for the high degree of hydrophilia of these materials, given that the cations tend to coordinate with water molecules. Thus, in addition to the olefin polymerization-related problems, these zeolites are seriously limited in their application in separation processes as a result of their high degree of hydrophilia, given that the water existing in the hydrocarbon currents, even at very low concentrations, tends to be adsorbed onto the cations located on the interior of the zeolite channels, thus decreasing the actual diameter of their pores.

Recently, Olson (D. H. Olson, U.S. Pat. No. 6,488,741 B2, 2002) has presented that zeolites that possess structures with pores formed by rings with a maximum of eight (8) members of tetrahedral can be selective for adsorbing propylene in the presence of propane. Thus, and more significantly, chabacite (CHA) and ITQ-3 (ITE) type structures are claimed.

In the present invention, it is shown how zeolite ITQ-32 (P200500245), which comprises pores formed by eight and twelve-member rings, makes it possible, thanks to its structure and topology, to preferentially adsorb propylene over propane and, in general, olefins over paraffins provided that their size make diffusion possible.

DESCRIPTION OF THE INVENTION

Zeolites can be classified as extra-large, large, medium or small-pore zeolites according to the opening of their channels. Thus, small-pore zeolites will have channels with openings formed by eight tetrahedral, while the medium-pore zeolites will be of 10 tetrahedra, the large ones of 12 and, lastly, the extra-large ones will have channels with openings of over 12 tetrahedra.

However, there are zeolites which possess more than one type of pore. Hence, for example, zeolite Nu-87 (Shannon, M. D., Casci, J. L., Cox, P. A. and Andrews, S. J. "Structure of the 2-Dimensional Medium-Pore High-Silica Zeolite NU-87", Nature 353, 417-420 (1991)) is characterized by a system of pores formed by rings of 10 tetrahedra and other pores formed by rings of 12 tetrahedra. Thus, in all scientific literature this zeolite is considered to be formed by pores of 10×12 MR (member rings). To the contrary, in the case of zeolite ZSM-5, all of the pores are formed by rings of 10 tetrahedra, it being considered a 10 MR zeolite.

For its utilization in the present invention, a zeolite has been synthesized which is called ITQ-32 and which, after being calcined for eliminating the organic compounds occluded in its interior, possesses an X-ray diffraction pattern which is unique and displays at least the angle $2\theta$ (degrees) and relative intensity ($I/I_0$) values stated in Table I.

TABLE I

| $2\theta$ (degrees) ± 0.5 | Intensity ($I/I_0$) |
| --- | --- |
| 7.4 | vs |
| 8.9 | vs |
| 12.9 | w |
| 19.5 | w |
| 20.3 | m |
| 20.9 | m |
| 22.0 | m |
| 24.3 | w |
| 26.0 | w |
| 27.1 | m |
| 27.6 | w |

Where "w" is a weak relative intensity of 0-20%, "m" is a medium relative intensity of 20-40% and "vs" is a very strong relative intensity of 60-100%.

The assay of the structure of the ITQ-32 zeolite shows the presence of pores formed by rings of eight tetrahedra and pores formed by rings of 12 tetrahedra. More specifically, the pores formed by rings of eight tetrahedra are connected with one another by way of pores with rings of 12 tetrahedra which interconnect adjacent and parallel pores of 8 tetrahedra.

This zeolite can be synthesized in a wide range of compositions and, in any case, T(IV)/T(III) ratios of over 10, T(IV)/T(III) ratios of over 200 and T(IV)/T(III) ratios of over 2000, where T(IV) refers to the tetravalent elements which conform the structure and T(III) to trivalent elements which could isomorphically substitute other tetravalent one in the network of the zeolite.

The present invention relates to a method of separating fluids which is characterized in that it comprises:
 a. bringing the ITQ-32 zeolite material into contact with the mixture of fluids,
 b. adsorption of one or more of the components into the ITQ-32 zeolite material,
 c. extraction of the non-adsorbed components, and
 d. recovery of one or more of the components adsorbed into the ITQ-32 zeolite material.

According to one preferred embodiment, said procedure comprises:
 a. bringing the ITQ-32 zeolite material into contact with the mixture of fluids selected from among:
  at least two hydrocarbons,
  a mixture comprised of at least methane and carbon dioxide,
  a mixture comprised of at least nitrogen and oxygen,
 b. adsorption of one or more of the components into the ITQ-32 zeolite material
 c. extraction of the non-adsorbed components, and
 d. recovery of one or more of the components adsorbed into the ITQ-32 zeolite material.

The separation method of this invention involves a certain quantity of ITQ-32 zeolite being brought into contact with a mixture of fluids, one or more of which are the desired fluids or, to the contrary, one or more are undesired, and which are preferably adsorbed into the interior of the ITQ-32 zeolite. The components of said mixture can be in gas phase or in liquid phase. The mixture and the ITQ-32 zeolite are kept in contact for the necessary length of time to make it possible for the adsorption process to take place and, lastly, the mixture of components which have not been adsorbed is extracted. The component or components adsorbed into the zeolite are recovered to subsequently be utilized or eliminated, depending on whether they are desired or undesired products. The recovery of said adsorbed components can be carried out by means of techniques such as entrainment with another gas, temperature rise, evacuation or combination of the aforementioned methods, among others.

According to one particular embodiment, in the stage of recovering the component or components adsorbed, the component or components which have preferentially been adsorbed are recovered.

According to another particular embodiment, in the stage of recovering the component or components adsorbed, the component or components which have preferentially not been adsorbed are recovered.

The efficiency of an adsorbent in separation processes is determined based on the value of the quotient of the diffusion coefficients of the by-products which are intended to be separated, referred to as $R_D$.

In the present invention, the method is characterized in that the ITQ-32 zeolite material utilized displays a diffusion rate faster than the component which is preferentially adsorbed, compared to that which is not preferentially adsorbed.

According to the method of the present invention, the quotient of the diffusion coefficients ($R_D$) of the components which separate in the ITQ-32 zeolite is preferably greater than 50, more preferably greater than 100 and more preferably greater than 1000.

According to one particular embodiment, the diffusion coefficients differ greatly between linear and branched hydrocarbons, preferably between linear and branched olefins, and also between olefins and paraffins, which makes their application in said hydrocarbon separation processes possible.

In addition to the above, the ITQ-32 zeolite material utilized in the method of the present invention is characterized in that it comprises a low content in trivalent elements in its composition. It can also be characterized by the absence of these trivalent elements.

According to one preferred embodiment, the ITQ-32 zeolite material displays a T(IV)/T(III) ratio of greater than 10. More preferably, said T(IV)/T(III) ratio is greater than 200. Yet more preferably, said T(IV)/T(III) ratio is greater than 2000.

According to one particular embodiment of the present invention, the mixture of fluids also comprises water.

Another important parameter in the adsorption properties of the zeolites is their adsorption capacity in equilibrium, which can be stated as weight of component adsorbed per unit of weight of adsorbent.

In one particular embodiment in which the fluids comprise hydrocarbons, the state of equilibrium is reached when the quantity of adsorbate does not increase over time under fixed conditions of hydrocarbon pressure and temperature. In principle, the greater the adsorption capacity of a zeolite, the smaller the quantity of zeolite will be required for separating a given quantity of hydrocarbon mixture.

Thus, in order for a certain fluid separation process to be feasible at the practical level, it is required that the zeolites have high $R_D$ values and high or moderate adsorption capacities.

The adsorption capacity of the component which is preferentially adsorbed into the ITQ-32 zeolite according to the method of the present invention varies in terms of the temperature and the pressure of said method.

According to one particular embodiment, the adsorption capacity at 25° C. and at vapor pressure at this temperature of the gas which is adsorbed is greater than 4.5% by weight.

In the present invention, it is shown that ITQ-32 zeolite of a low content in trivalent elements in its composition, and even in absence thereof, displays different diffusion rates in the adsorption kinetics of different gases.

According to one particular embodiment, said gases can be hydrocarbons, such as, for example, propane/propene. According to this embodiment, the ITQ-32 zeolite material displays a propene adsorption capacity at 800 mbar and 60° C. nearing 4% by weight for adsorption times of three minutes, the adsorption of propane under these conditions being on the order of 0.2%. Based on these results, it can be concluded that ITQ-32 zeolite is a highly suitable adsorbent for carrying out propene and propane separation processes and, in general, for olefin/paraffin or hydrocarbon systems in general which may diffuse through its pores.

According to another particular embodiment, the ITQ-32 zeolite with a low content in trivalent elements in its composition or even in absence thereof displays an adsorption capacity of less than 0.5% by weight for branched olefins even under conditions of equilibrium, which makes its use possible also for processes of separating linear from branched hydrocarbons, preferably linear from branched olefins.

The ITQ-32 zeolite employed in the method of the present invention has a water adsorption capacity of less than 1% by weight, which demonstrates its hydrophobic nature, permitting the separation of fluids in the presence of major quantities of water.

This separation process can also be carried out in columns, in which case different product faces are obtained depending on whether they are retained more or less strongly by the ITQ-32 zeolite bed.

According to one particular embodiment, the mixture of fluids of the present invention is a mixture of at least two hydrocarbons. These hydrocarbons preferably comprise at least one olefin and one paraffin.

According to one particular embodiment, the olefin is selected from among ethene, propene, 1-butene, trans-2-butene, cis-2-butene, 1,4-butadiene, isobutene and combinations of the same, and the paraffin is selected from among ethane, propane, n-butane and combinations of the same.

According to one preferred embodiment, the olefin is propene, and the paraffin is propane.

According to another preferred embodiment, the olefin is selected from among 1-butene, trans-2-butene, cis-2-butene, 1,4-butadiene, isobutene and combinations of the same, and the paraffin is n-butane.

These preferred embodiments, in which the mixture of fluids comprises at least one olefin and one paraffin, are characterized in that the olefin is the component which is preferentially adsorbed, while the paraffin is the component which is preferentially not adsorbed.

Another preferred embodiment is that in which the mixture of fluids comprises at lease one linear hydrocarbon and at least one branched hydrocarbon. According to this embodiment, the linear hydrocarbon is the component which is preferentially adsorbed, and the branched hydrocarbon is that component which is preferentially not adsorbed.

Another particular embodiment is that in which the mixture of fluids comprises at least two olefins. According to one preferred embodiment, said olefins are trans-2-butene and cis-2-butene. According to this preferred embodiment, the trans-2-butene is that which is preferentially adsorbed, and the cis-2-butene is the component which is not preferentially adsorbed.

According to another particular embodiment in which the mixture of fluids comprises at least 2 olefins, said olefins are preferably 1-butene and isobutene. According to this particular embodiment, the 1-butene is the component which is preferentially adsorbed, and the isobutene is the component which is preferentially not adsorbed.

The embodiments of the present invention in which the mixture of fluids is preferably a mixture of hydrocarbons are characterized in that they are carried out within a temperature range of −100° C. and 300° C., preferably within −30° C. and 200° C.

According to another preferred embodiment, said fluids are methane and $CO_2$. This method is carried out preferably within a temperature range of −196° C. and 150° C.

According to one preferred embodiment, the fluid separation method of the present invention is characterized in that said fluids are nitrogen and oxygen in mixtures of air.

According to the method of the present invention, the process of separating and recovering the desired gas can be carried out by at least one of the processes selected from among pressure swing adsorption (PSA), multi-stage pressure swing adsorption (multi-stage PSA), single-stage membrane separation, multi-stage membrane separation and a flow type system. These techniques can be utilized independently of the content of the initial fluid mixture.

According to the particular embodiment in which the fluids are hydrocarbons, the separating conditions will depend on the exact composition of the fluids to be separated, preferably having an upper temperature limit corresponding to the start of the thermal cracking reaction of the hydrocarbons and a lower limit corresponding to its freezing point. Thus, the procedure of this particular embodiment of this invention must be carried out between −100° C. and 300° C., preferably between −30° C. and 200° C.

Another preferred embodiment, in which the ITQ-32 zeolite with a T(IV/T(III) ratio of over 10, preferably of over 200 and more preferably of over 2000 is employed is the separation of nitrogen and oxygen from mixtures of air and separation of methane and $CO_2$. Given that the ITQ-32 zeolite employed in this invention is characterized by being highly hydrophobic, it permits the separation of nitrogen and oxygen in mixtures of air, as well as of methane and $CO_2$. in the presence of water.

In following, as examples, the preparation of some samples of ITQ-32 and the separation properties of different gases employing an ITQ-32 zeolite of a high T(IV)/T(III) ratio are presented. For this purpose, the adsorption capacity and rate of propene and propane at various pressures and temperatures has been determined. The examples which are described in following are not intended to be limiting as regards the scope of the invention.

EXAMPLES

Example 1

Preparation of the ITQ-32 Material of a T(IV)/T(III)=35

0.151 g Al isopropoxide is added onto 7.88 g tetraethylorthosilicate (TEOS). Next, 20.08 g of 4-cyclohexyl-1,1-dimethyl-piperazinium hydroxide (R'(OH)) solution which contains 1 hydroxide equivalent in 1000 g are added. The mixture is left evaporating while stirred up to complete elimination of the ethanol from the hydrolysis of the TEOS plus the amount of water necessary up to obtaining the final composition indicated. Lastly, 0.80 g of a fluorhydric acid (50% HF by weight) is added. The composition of the gel is:

The mixture obtained is placed inside a polytetrafluoroethylene-lined autoclave and is heated to 175° C. for 6 days in an oven equipped with a rotation system. The solid obtained on filtering, washing with distilled water and drying at 100° C. is ITQ-32.

Example 2

Preparation of the ITQ-32 Material of a T(IV)/T(III)=260

Figure 1:
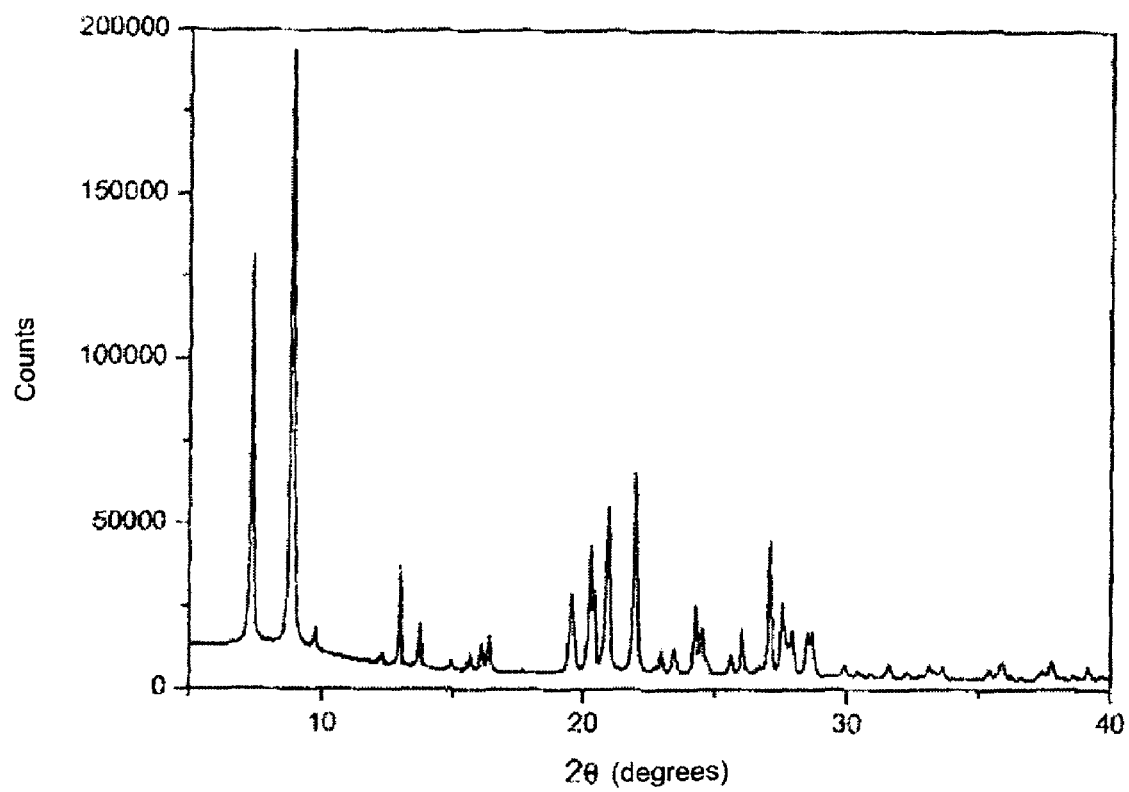
FIG. 1. X-ray diffraction diagram of the ITQ-32 zeolite of an Si/Al ratio=260 prepared according to example 2.

7.86 g tetraethylorthosilicate (TEOS) is added onto 20 g of a 4-cyclohexyl-1,1-dimethyl-piperazinium hydroxide (R'(OH)) solution which contains 1 hydroxide equivalent in 1000 g. The mixture is left evaporating while stirred up to complete elimination of the ethanol from the hydrolysis of the TEOS plus the amount of water necessary up to obtaining the final composition indicated. Lastly, 0.80 g of a fluorhydric acid (50% HF by weight) and a suspension in water of 0.22 g ITQ-32 zeolite prepared exactly as described in Example 1 is added. The composition of the gel is:

$SiO_2$: 0.00105 $Al_2O_3$: 0.54 R'(OH): 0.54 HF: $7H_2O$

Where the aluminum that is incorporated into the synthesis gel comes from the ITQ-32 zeolite employed as the seeding material. The mixture obtained is placed inside a polytetrafluoroethylene-lined autoclave and is heated to 175° C. for 2 days in an oven equipped with a rotation system. The solid obtained on filtering, washing with distilled water and drying at 100° C. is ITQ-32. The calcination at 580° C. in air for 3 hours makes it possible to eliminate the occluded organic species and to obtain the ITQ-32 material capable of being used in adsorption and separation processes. The X-ray diagram of the sample obtained in its calcined form is shown in FIG. 1.

Example 3

Adsorption of Propene at 25° C. into the ITQ-32 Material of Example 2

The measurement of the propene adsorption capacity of the ITQ-32 material prepared according to Example 2, at 25° C. and 900 mbar corresponds to 5.5% by weight. Similarly, the value obtained after carrying out 20 adsorption/desorption cycles is of 5.3% by weight, which demonstrates that the ITQ-32 material retains its adsorption capacity indicating that oligomerization processes which block the pores of the zeolite do not take place.

Example 4

Adsorption of Propene at 60° C. into the ITQ-32 Material of Example 2

The measurement of the propene adsorption capacity of the ITQ-32 material prepared according to Example 2 at 60° C. and 900 mbar corresponds to 5.1% by weight.

Example 5

Propane Adsorption at 60° C. into the ITQ-32 Material of Example 2

The measurement of the propane adsorption capacity of the ITQ-32 material prepared according to Example 2 at 60° C. and 900 mbar corresponds to 2.5% by weight after balancing for three hours at this temperature and pressure without any constant weight being achieved.

Example 6

Propane Adsorption at 25° C. into the ITQ-32 Material of Example 2

The measurement of the propane adsorption capacity of the ITQ-32 material prepared according to Example 2 at 25° C. and 900 mbar corresponds to 1.85% by weight after balancing for three hours at this temperature and pressure without any constant weight being achieved. The lesser adsorption capacity under these conditions in comparison to that found in Example 5 indicates the low diffusion capacity of the propane through the pores of the ITQ-32 zeolite.

Example 7

Determination of Propene/Propane Diffusion Coefficient $R_D$ at 60° C. and 800 mbar in the ITQ-32 Material of Example 2

Figure 2:
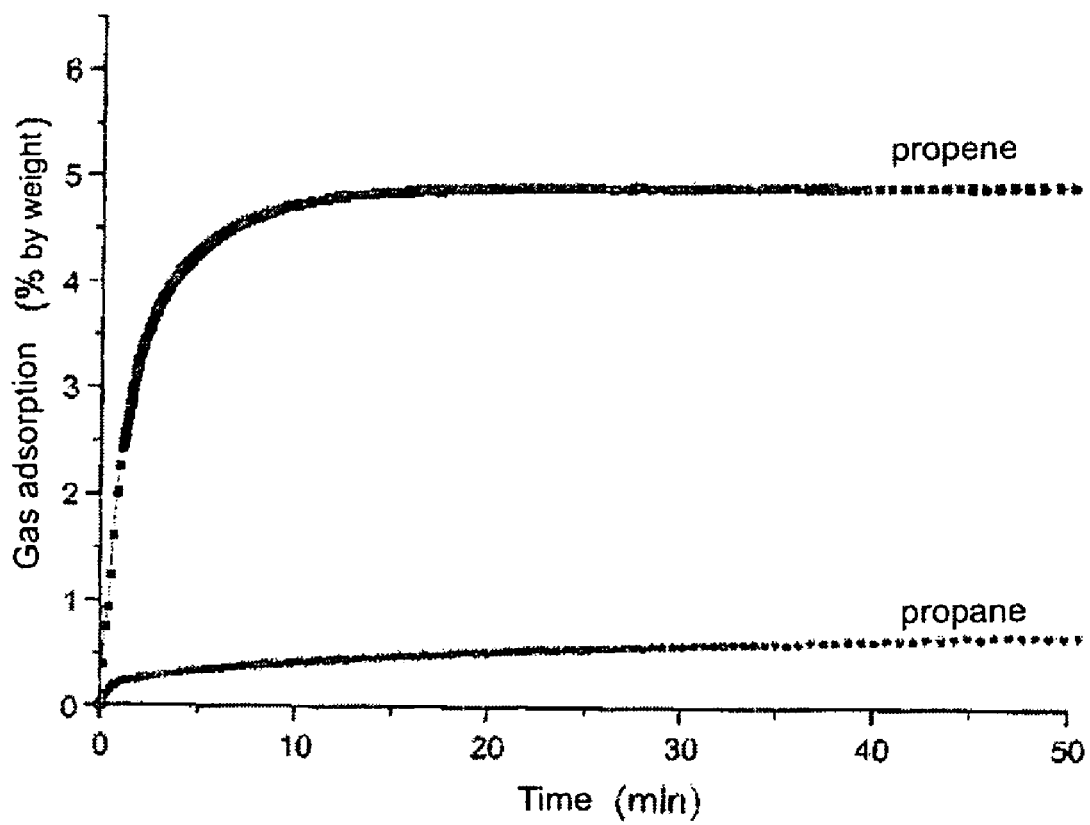
FIG. 2. Adsorption curves of propane and propene as a function of time in an ITQ-32 zeolite of an Si/Al ratio=260 at 60° C. and an adsorbate pressure of 800 mbar.

The propene and propane adsorption in terms of the time into the ITQ-32 material prepared according to Example 2 at 60° C. and 800 mbar is shown in FIG. 2.

From these curves, the relative coefficients of the diffusion rates of both products in the ITQ-32 zeolite can be calculated. For this purpose, the parameter $D/r^2$, where "D" is the diffusion coefficient and "r" is the radius of the particle, the kinetic adsorption measurements are obtained assuming a flat laminar diffusion model which approximately describes the process. Thus, for a quantity of adsorbate, Q, the value $Q/Q_\infty$, where $Q_\infty$ is the quantity of adsorbate adsorbed in 1 equilibrium, is mathematically related to $(Dt/r^2)^{0.5}$, where "t" is the time in seconds required for a quantity "Q" of the sample to be adsorbed (J. Crank in The mathematics of diffusion, Clarendon Press, Oxford, UK, 1975). The relative diffusion coefficients $(D/r^2)$ obtained in the ITQ-32 zeolite synthesized according to Example 2 were $7.49 \times 10^{-3}$ and $5.06 \times 10^{-6}$ $s^{-1}$ for the propene and propane, respectively; the quotient between them ($R_D$) being 1481.

Example 8

Determination of Propene/Propane Diffusion Coefficient $R_D$ at 25° C. and 800 mbar in the ITQ-32 Material of Example 2

Figure 3:
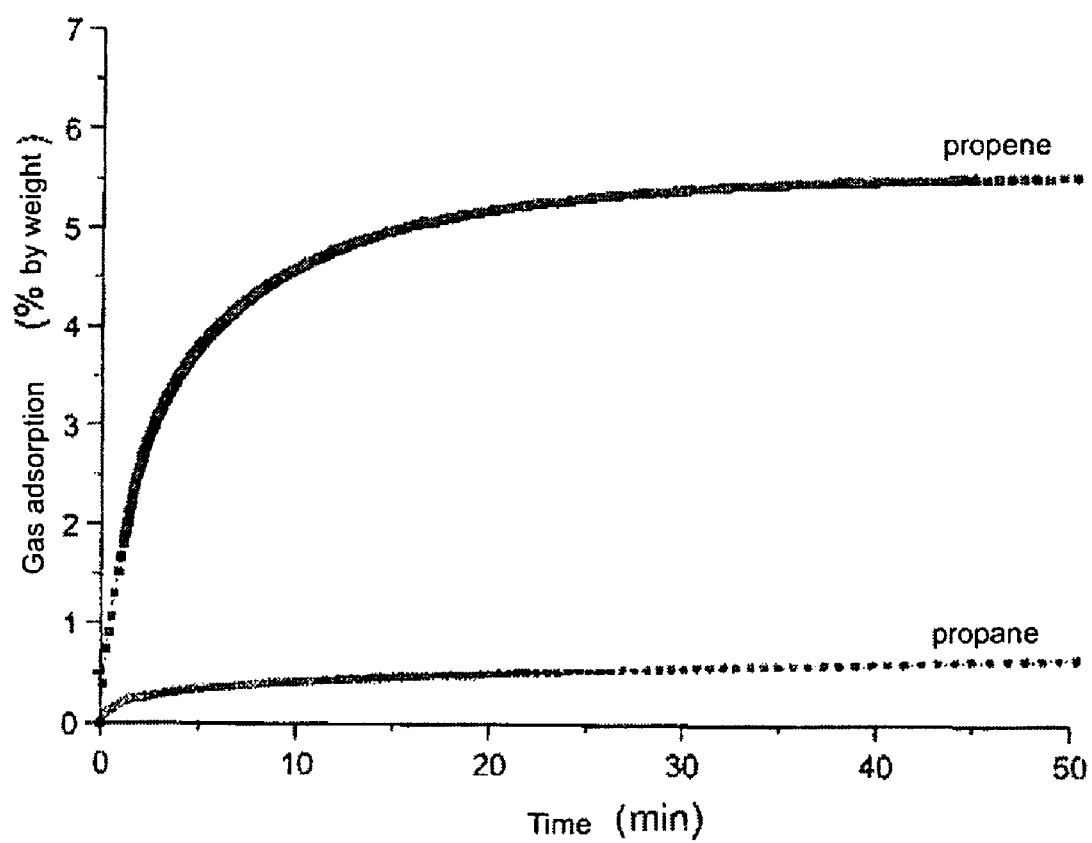
FIG. 3. Adsorption curves of propane and propene as a function of time in an ITQ-32 zeolite of an Si/Al ratio=260 at 25° C. and an adsorbate pressure of 800 mbar.

The propene and propane adsorption, as a function of time, into the ITQ-32 material prepared according to Example 2 at 25° C. and 800 mbar is shown in FIG. 3.

The relative diffusion coefficients of propane and propene, as well as the $R_D$ quotient was calculated as in Example 7. The relative diffusion coefficients $(D/r^2)$ obtained in the ITQ-32 zeolite synthesized according to Example 2 were $2.92 \times 10^{-3}$ and $1.72 \times 10^{-6}$ $s^{-1}$ for the propene and propane, respectively; the quotient between them ($R_D$) being 1698.

Example 9

Determination of Propene/Propane Diffusion Coefficient $R_D$ at 25° C. and 300 mbar in the ITQ-32 Material of Example 2

Figure 4:
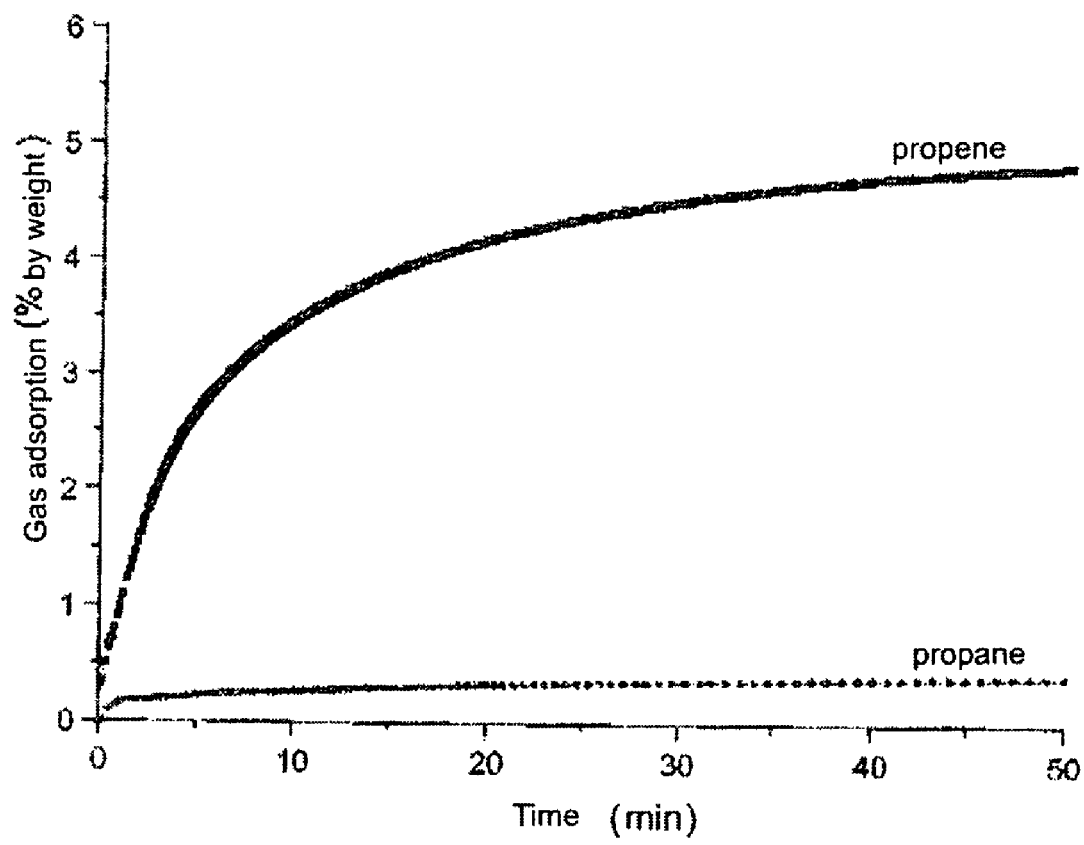
FIG. 4. Adsorption curves of propane and propene as a function of time in an ITQ-32 zeolite of an Si/Al ratio=260 at 25° C. and an adsorbate pressure of 300 mbar.

The propene and propane adsorption, as a function of time, into the ITQ-32 material prepared according to Example 2 at 25° C. and 300 mbar is shown in FIG. 4.

The relative diffusion coefficients of propane and propene, as well as the $R_D$ quotient was calculated as in Example 7. The relative diffusion coefficients $(D/r^2)$ obtained in the ITQ-32 zeolite synthesized according to Example 2 were $1.35 \times 10^{-3}$ and $7.02\times10^{-7}$ s$^{-1}$ for the propene and propane, respectively; the quotient between them ($R_D$) being 1923.

Example 10

Determination of Propene/Propane Diffusion Coefficient $R_D$ at 25° C. and 100 mbar in the ITQ-32 Material of Example 2

Figure 5:
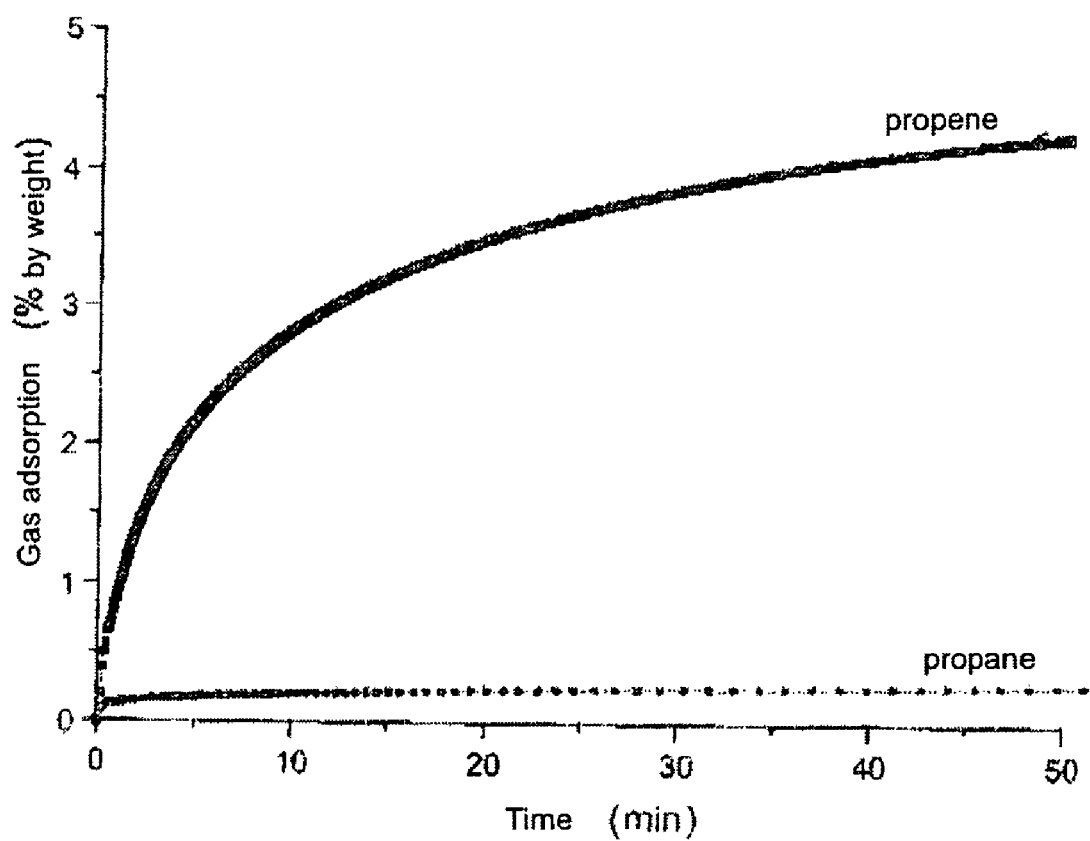
FIG. 5. Adsorption curves of propane and propene as a function of time in an ITQ-32 zeolite of an Si/Al ratio=260 at 25° C. and an adsorbate pressure of 100 mbar.

The propene and propane adsorption, as a function of time, into the ITQ-32 material prepared according to Example 2 at 25° C. and 100 mbar is shown in FIG. 5.

The relative diffusion coefficients of propane and propene, as well as the $R_D$ quotient was calculated as in Example 7. The relative diffusion coefficients (D/r$^2$) obtained in the ITQ-32 zeolite synthesized according to Example 2 were $1.05\times10^{-3}$ and $2.98\times10^{-7}$ s$^{-1}$ for the propene and propane, respectively; the quotient between them ($R_D$) being 3523.

Example 11

Determination of the Adsorption Capacity of iso-butene at 25° C. into the ITQ-32 Material of Example 2

The measurement of the isobutene adsorption capacity of the ITQ-32 material prepared according to Example 2 at 25° C. and 900 mbar corresponds to 0.27% by weight.

The invention claimed is:

1. A method of separating fluids comprising:
  a. bringing an ITQ-32 zeolite material into contact with a mixture of fluids, each fluid comprising at least one component,
  b. adsorption of one or more of the components of the fluids into the ITQ-32 zeolite material,
  c. extraction of the non-adsorbed components, and
  d. recovery of one or more of the components adsorbed into the ITQ-32 zeolite material.

2. The method of separating fluids according to claim 1, comprising:
  a. bringing the ITQ-32 zeolite material into contact with the mixture of fluids, each fluid comprising at least one component, wherein the mixture of fluids is selected from the up consisting of:
    at least two hydrocarbons,
    a mixture comprising at least methane and carbon dioxide, and
    a mixture comprising at least nitrogen and oxygen,
  b. adsorption of one or more of the components of the fluids into the ITQ-32 zeolite material
  c. extraction of the non-adsorbed components, and
  d. recovery of one or more of the components adsorbed into the ITQ-32 zeolite material.

3. The method of separating fluids according to claim 1, wherein the ITQ-32 zeolite material displays a faster diffusion rate for a component which is preferentially adsorbed in comparison to that which is not preferentially adsorbed.

4. The method of separating fluids according to claim 1, wherein the ITQ-32 zeolite material displays a T(IV)/T(III) ratio of greater than 10.

5. The method of separating fluids according to claim 4, wherein the ITQ-32 zeolite material displays a T(IV)/T(III) ratio of greater than 200.

6. The method of separating fluids according to claim 4, wherein the ITQ-32 zeolite material displays a T(IV)/T(III) ratio of greater than 2000.

7. The method of separating fluids according to claim 1, wherein the mixture of fluids further comprises water.

8. The method of separating fluids according to claim 1, wherein a quotient of the diffusion coefficients, $R_D$, of the components which are separated in the ITQ-32 zeolite material is greater than 50.

9. The method of separating fluids according to claim 8, wherein the quotient of the diffusion coefficients, $R_D$, of the components which are separated in the ITQ-32 zeolite material is greater than 100.

10. The method of separating fluids according to claim 8, wherein the quotient of the diffusion coefficients, $R_D$, of the components which are separated in the ITQ-32 zeolite material is greater than 1000.

11. The method of separating fluids according to claim 1, wherein the component or components which are recovered are the component or components preferentially adsorbed.

12. The method of separating fluids according to claim 1, wherein the component or components which are recovered are the component or components preferentially not adsorbed.

13. The method of separating fluids according to claim 1, wherein the mixture of fluids is a mixture of at least two hydrocarbons.

14. The method of separating fluids according to claim 13, wherein the mixture of at least two hydrocarbons is at least one olefin and one paraffin.

15. The method of separating fluids according to claim 14, wherein the olefin is selected from the group consisting of ethene, propene, 1-butene, trans-2-butene, cis-2-butene, 1,4-butadiene, isobutene and combinations thereof.

16. The method of separating fluids according to claim 14, wherein the paraffin is selected from the group consisting of ethane, propane, n-butane and combinations thereof.

17. The method of separating fluids according to claim 14, wherein the olefin is propene and the paraffin is propane.

18. The method of separating fluids according to claim 14, wherein the olefin is selected from the group consisting of 1-butene, trans-2-butene, cis-2-butene, 1,4-butadiene, isobutene and combinations thereof, and the paraffin is n-butane.

19. The method of separating fluids according to claim 14, wherein the olefin is the component that is preferentially adsorbed, and the paraffin is the component which is preferentially not adsorbed.

20. The method of separating fluids according to claim 13, wherein the mixture of at least two hydrocarbons is at least one linear hydrocarbon and at least one branched hydrocarbon.

21. The method of separating fluids according to claim 20, wherein the linear hydrocarbon is the component that is preferentially adsorbed, and the branched hydrocarbon is the component which is preferentially not adsorbed.

22. The method of separating fluids according to claim 13, wherein the mixture of at least two hydrocarbons is at least two olefins.

23. The method of separating fluids according to claim 22, wherein the olefins are trans-2-butene and cis-2 butene.

24. The method of separating fluids according to claim 23, wherein the trans-2-butene is the component that is preferentially adsorbed, and the cis-2-butene is the component which is preferentially not adsorbed.

25. The method of separating fluids according to claim 22, wherein the olefins are 1-butene and isobutene.

26. The method of separating fluids according to claim 25, wherein the 1-butene is the component that is preferentially adsorbed, and the isobutene is the component which is preferentially not adsorbed.

27. The method of separating fluids according to claim 13, which it is carried out within a temperature range of −100° C. and 300° C.

28. The method of separating fluids according to claim 27, which it is carried out within a temperature range of −30° C. and 200° C.

29. The method of separating gases fluids according to claim 1, wherein the mixture of fluids comprises methane and $CO_2$.

30. The method of separating fluids according to claim 29, which it is carried out within a temperature range of −196° C. and 150° C.

31. The method of separating fluids according to claim 1, wherein the mixture of fluids comprises nitrogen and oxygen in mixtures of air.

32. The method of separating fluids according to claim 1, wherein the recovery of the one or more components is carried out by at least one process selected from the group consisting of PSA, multi-stage PSA, single-step membrane separation, multi-step membrane separation, flow type system and combinations thereof.

33. The method of separating fluids according to claim 32, wherein the component which is recovered is propene.

34. The method of separating fluids according to claim 32, wherein the component which is recovered is selected from the group consisting of 1-butene, trans-2-butene, cis-2-butene, 1,4-butadiene, isobutene and combinations thereof.

35. The method of separating fluids according to claim 32, wherein the component which is recovered is a linear hydrocarbon.

36. The method of separating fluids according to claim 32, wherein the component which is recovered is trans-2-butene.

37. The method of separating fluids according to claim 32, wherein the component which is recovered is 1-butene.

38. The method of separating fluids according to claim 32, wherein the component which is recovered is methane.

39. The method of separating fluids according to claim 32, wherein the component which is recovered is nitrogen.

* * * * *